US011071458B2

(12) United States Patent
Unnimadhava Kurup Soudamini Amma et al.

(10) Patent No.: US 11,071,458 B2
(45) Date of Patent: Jul. 27, 2021

(54) SERS-ACTIVE OPTO-FLUIDIC PHOTONIC CRYSTAL FIBER PROBE AS BIOPSY NEEDLE AND OPTOFLUIDIC SENSOR

(71) Applicants: Agency for Science, Technology and Research, Singapore (SG); Centre National De La Recherche Scientifique (CNRS), Paris (FR); Université De Limoges, Limoges (FR)

(72) Inventors: Dinish Unnimadhava Kurup Soudamini Amma, Singapore (SG); Malini Olivo, Singapore (SG); Georges Humbert, Paris (FR); Perumal Jayakumar, Singapore (SG)

(73) Assignees: Agency for Science, Technology and Research, Singapore (SG); Centre National De La Recherche Scientifique (CNRS); Université De Limoges

(*) Notice: Subject to any disclaimer, the term of this patent is extended or adjusted under 35 U.S.C. 154(b) by 0 days.

(21) Appl. No.: 16/622,882

(22) PCT Filed: Jul. 2, 2018

(86) PCT No.: PCT/SG2018/050323
§ 371 (c)(1),
(2) Date: Dec. 13, 2019

(87) PCT Pub. No.: WO2019/004944
PCT Pub. Date: Jan. 3, 2019

(65) Prior Publication Data
US 2020/0205667 A1 Jul. 2, 2020

(30) Foreign Application Priority Data

Jun. 30, 2017 (SG) .......................... 10201705412Q

(51) Int. Cl.
*A61B 5/1459* (2006.01)
*G01J 3/44* (2006.01)
(Continued)

(52) U.S. Cl.
CPC .......... *A61B 5/0075* (2013.01); *A61B 5/1459* (2013.01); *A61B 5/6848* (2013.01);
(Continued)

(58) Field of Classification Search
CPC ..... G01J 3/44; G01N 21/658; G02B 6/02323; A61B 5/0075; A61B 5/1459; A61B 5/6848; A61B 10/0233
See application file for complete search history.

(56) References Cited

U.S. PATENT DOCUMENTS 5,864,397 A    1/1999   Vo-Dinh
5,983,125 A * 11/1999   Alfano ................ A61B 5/0075
                                                          600/473
(Continued)

FOREIGN PATENT DOCUMENTS

| CN | 105943055 A | 9/2016 |
| WO | 2011155901 A1 | 12/2011 |
| WO | 2015114379 A1 | 8/2015 |

OTHER PUBLICATIONS

Xuan Yang, "Hollow-Core Photonic Crystal Fibers for Surface-Enhanced Raman Scattering Probes", 2011 (Year: 2011).*
(Continued)

*Primary Examiner* — Maurice C Smith
(74) *Attorney, Agent, or Firm* — Winstead PC

(57) ABSTRACT

The present application discloses a surface-enhanced Raman scattering (SERS)-active photonic crystal fiber (PCF) probe including a biopsy needle in the PCF probe for integrated sample collection and SERS sensing of one or more analytes comprised in the sample. The PCF comprises solid core and
(Continued)

a cladding region surrounding the solid core, wherein the cladding region comprises air holes functionalised by metallic nanoparticles. The application also provides a method for detecting one or more analytes using the PCF probe as well as the use of the PCF probe for the detection of one or more analytes.

20 Claims, 8 Drawing Sheets

(51) Int. Cl.
| | |
|---|---|
| A61B 5/00 | (2006.01) |
| A61B 10/02 | (2006.01) |
| G01J 3/02 | (2006.01) |
| G01N 21/65 | (2006.01) |
| G02B 6/02 | (2006.01) |

(52) U.S. Cl.
CPC ........ *A61B 10/0233* (2013.01); *G01J 3/0218* (2013.01); *G01J 3/44* (2013.01); *G01N 21/658* (2013.01); *G02B 6/02333* (2013.01); *G02B 6/02361* (2013.01); *A61B 2562/0233* (2013.01); *A61B 2562/0285* (2013.01)

(56) References Cited

U.S. PATENT DOCUMENTS

| | | | |
|---|---|---|---|
| 6,174,291 B1 * | 1/2001 | McMahon | A61B 5/0071 600/564 |
| 7,761,139 B2 * | 7/2010 | Tearney | A61B 5/6852 600/473 |
| 9,001,324 B2 | 4/2015 | Li et al. | |
| 2004/0249268 A1 | 12/2004 | Da Silva | |
| 2007/0020144 A1 | 1/2007 | Du et al. | |
| 2010/0317964 A1 | 12/2010 | Hendriks et al. | |
| 2011/0176130 A1 * | 7/2011 | Gu | G02B 6/02385 356/301 |
| 2011/0319759 A1 | 12/2011 | Liu et al. | |
| 2014/0316255 A1 * | 10/2014 | Garai | G01J 3/18 600/424 |
| 2015/0223739 A1 | 8/2015 | Walavalkar et al. | |
| 2016/0067666 A1 | 3/2016 | Walavalkar et al. | |
| 2016/0169886 A1 * | 6/2016 | Chou | G01N 33/553 506/9 |
| 2016/0178439 A1 | 6/2016 | Freudiger et al. | |
| 2016/0231337 A1 * | 8/2016 | Olivo | B82Y 15/00 |
| 2017/0173275 A1 | 6/2017 | Anderson et al. | |

OTHER PUBLICATIONS

Stevens, Oliver, "A low background Raman probe for optical biopsy of brain tissue", 2014 (Year: 2014).*
John Day, "A Subcutaneous Raman Needle Probe" Society for Applied Spectroscopy, 2013 (Year: 2013).*
International Search Report for International Application No. PCT/SG2018/050323 dated Sep. 28, 2018, pp. 1-6.
Written Opinion of the International Searching Authority for International Application No. PCT/SG2018/050323 dated Sep. 28, 2018, pp. 1-6.
Zysk et al., "Clinical Feasibility of Microscopically-Guided Breast Needle Biopsy Using a Fiber-Optic Probe with Computer-Aided Detection," Technology in Cancer Research and Treatment, vol. 8, No. 5, Oct. 2009, pp. 315-321.
Pinkhasova, et al., "Nanotag-Enabled Photonic Crystal Fiber as Quantitative Surface-Enhanced Raman Scattering Optofluidic Platform," Applied Physics Letters, vol. 106, Mar. 11, 2015, pp. 071106, pp. 1-4.
Oo et al., "Structure Fits the Purpose: Photonic Crystal Fibers for Evanescent-Field Surface-Enhanced Raman Spectroscopy," Optics Letters, vol. 35, No. 4, Feb. 15, 2010, pp. 466-468.
Dinish et al., "Highly Sensitive SERS Detection of Cancer Proteins in Low Sample Volume Using Hollow Core Photonic Crystal Fiber," Biosensors and Bioelectronics, vol. 33, Jan. 4, 2012, pp. 293-298.
Dinish et al., "Sensitive Multiplex Detection of Serological Liver Cancer Biomarkers Using SERS—Active Photonic Crystal Fiber Probe," Journal of Biophotonics, vol. 7, No. 11-12, 2014, pp. 956-965.
Gong et al., "Highly Sensitive SERS Detection and Quantification of Sialic Acid on Single Cell Using Photonic-Crystal Fiber with Gold Nanoparticles," Biosensors and Bioelectronics, vol. 64, 2015, pp. 227-233.
Zhang et al., "Design and Fabrication of Side-Channel Photonic Crystal Fiber for Surface Enhanced Raman Scattering Applications," Optical Society of America, 2015, pp. 1-2.
Gong et al., "Rapid SERS Monitoring of Lipid-Peroxidation-Derived Protein Modifications in Cells Using Photonic Crystal Fiber Sensor," Journal of Biophonotics, vol. 9, No. 1-2, 2016, pp. 32-37.
Zhang et al., "Side-Channel Photonic Crystal Fiber for Surface Enhanced Raman Scattering Sensing," Sensors and Actuators B: Chemical, vol. 223, 2016, pp. 195-201.
Extended European Search Report for European Patent Application No. 18822592.4 dated Feb. 15, 2021, pp. 1-22.
Tan et al., "Near-Infrared Raman Spectroscopy Using Hollow-Core Photonic Bandgap Fibers," Optics Communications, vol. 283, 2010, pp. 3204-3206.

* cited by examiner (a) (b) (c)

(a) (b)

(a) (b)

(a)                                                                (b)

(a)  (b)

(a)

(b)

SERS-ACTIVE OPTO-FLUIDIC PHOTONIC CRYSTAL FIBER PROBE AS BIOPSY NEEDLE AND OPTOFLUIDIC SENSOR

CROSS-REFERENCE TO RELATED APPLICATION

This application refers to and claims the benefit of priority of the Singapore Patent Application No. 10201705412Q filed on 30 Jun. 2017, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to surface-enhanced Raman scattering (SERS)-active photonic crystal fiber (PCF) probes and methods of using the same.

BACKGROUND OF THE INVENTION

Surface enhanced Raman scattering (SERS) is a versatile sensing and analytical technique where an analyte is adsorbed onto a SERS-active substrate. Due to the surface plasmonic effect, the analyte molecules experience significant increase in field intensity; hence, the detectable scattering signal is also increased by several folds. A SERS spectrum of an analyte typically comprises peaks or bands, which uniquely represent a specific set of atomic groups/species present in the said analyte. This salient feature enables formation of a Raman spectrum of molecules that can represent the analyte's vibrational frequencies and offers a platform for the "fingerprint" characterization.

Incorporation of SERS phenomena along with conventional fibers with hollow cores have been tested as SERS platforms. However, there remains a considerable need for new technologies with improved technical properties.

SUMMARY OF THE INVENTION

The present invention satisfies the aforementioned need in the art by providing novel PCF probes and methods of using the same.

In one aspect, the present invention relates to a surface-enhanced Raman scattering (SERS)-active photonic crystal fiber (PCF) probe for integrated sample collection and SERS sensing of one or more analytes comprised in the sample, the probe comprising a biopsy needle and a SERS-active PCF integrated into or in communication with the biopsy needle, wherein the PCF has a longitudinal axis and comprises a solid core extending along the length of the longitudinal axis and a cladding region surrounding the solid core, wherein at least the cladding region comprises one or more air holes extending along the longitudinal axis of the PCF, wherein the inner surface of the one or more air holes is functionalized by metallic nanoparticles immobilized thereon that enhance Raman scattering, and the one or more air holes are adapted for SERS sensing of the one or more analytes.

In various embodiments, the core and the one or more air holes in the cladding region are arranged in a pattern as illustrated in any one of FIGS. 2-6 of the drawings.

In various embodiments, the inner surface of the one or more air holes comprises, consists essentially of or is made of silica glass.

In various embodiments, the metallic nanoparticles comprise or consist of a noble metal or copper.

In various embodiments, the noble metal is gold or silver.

In various embodiments, the metallic nanoparticles have a mean diameter in the range from 5 nm to 250 nm, preferably in the range from 40 nm to 100 nm.

In various embodiments, the metallic nanoparticles comprise or consist of gold nanoparticles preferably having a mean diameter of 60 nm.

In various embodiments, the metallic nanoparticles are immobilized onto the inner surface via a coupling agent, preferably a silane coupling agent, more preferably a molecule comprising a di- or trialkoxysilane group and a functional group capable of binding to the metallic nanoparticles, such as an amino or mercapto group, the coupling agent being preferably selected from (3-mercaptopropyl)trimethoxysilane (MPTMS) and 3-Aminopropyltriethoxysilane (APTES).

In various embodiments, the metallic nanoparticles are further functionalized by a first analyte-binding molecule immobilized thereon.

In various embodiments, the first analyte-binding molecule is an antibody, antibody fragment, or antibody-like molecule.

In various embodiments, the first analyte-binding molecule is a monoclonal or polyclonal antibody.

In another aspect, the invention relates to a method for detecting one or more analytes using surface-enhanced Raman scattering (SERS), the method comprising the steps of:
(i) loading a sample suspected of containing the one or more analytes into a SERS-active PCF probe disclosed herein via the biopsy needle comprised therein;
(ii) immobilizing the one or more analytes to the metallic nanoparticles coated on the one or more air holes of the PCF probe;
(iii) loading a second analyte-binding molecule comprising a Raman reporter moiety into the SERS-active PCF probe; and
(iv) detecting the one or more analytes by measuring a SERS signal from the SERS-active PCF probe.

In various embodiments, the method comprises an additional blocking step immediately prior to step (ii).

In various embodiments, the method comprises an additional washing step immediately prior to step (iii) and/or (iv) to remove the unbound analytes and/or analyte-binding molecules, respectively.

In various embodiments, the sample is a body fluid or biological fluid.

In various embodiments, the sample is selected from the group consisting of whole blood, serum, plasma, cerebrospinal fluid, sputum, bronchial washing, bronchial aspirates, urine, semen, lymph fluids, wound exudates, tears, saliva, milk, and cell culture supernatants.

In various embodiments, the one or more analytes are selected from the group consisting of proteins, peptides, nucleic acids, carbohydrates, lipids, small molecules, haptens, cells, and viruses.

In various embodiments, the second analyte-binding molecule is an antibody, antibody fragment, or antibody-like molecule.

In various embodiments, the second analyte-binding molecule is a monoclonal or polyclonal antibody.

In various embodiments, the Raman reporter moiety comprised in the second analyte-binding molecule selected from the group consisting of malachite green isothiocyanate (MGITC), tetramethylrhodamine-5-isothiocyanate (TRITC), X-rhodamine-5-(and-6)-isothiocyanate (XRITC), and 3, 3'-diethylthiadicarbocyanine iodide (DTDC).

In various embodiments, the method is a multiplex method for detecting more than one analyte, wherein in the contacting step more than one analyte-binding molecule is used.

In various embodiments, the detection is in vivo or in vitro.

In still another aspect, the invention relates to the use of the SERS-active PCF probe disclosed herein for the detection of one or more analytes.

In various embodiments, the detection is in vivo or in vitro.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
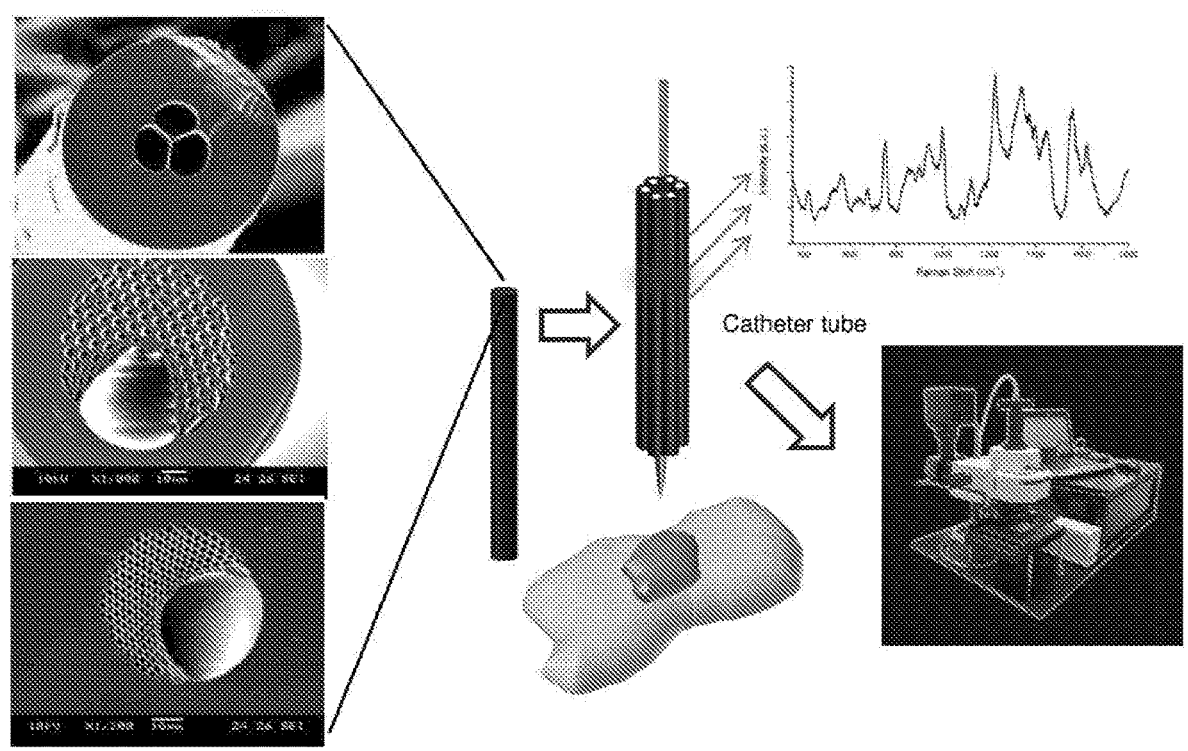
FIG. 1 shows a general design of the PCF probe.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a," "an," and "the" include plural referents unless context clearly indicates otherwise. The terms "at least one" or "one or more" as used interchangeably herein mean 1, 2, 3 or more, for example at least 1, 2, 3, 4, 5, 6, 7, 8, 9, 10, 12, 14, 15, 20, 25 or more. In this connection, the term "plurality" means more than two, preferably 3-100. Similarly, the word "or" is intended to include "and" unless the context clearly indicates otherwise. The term "comprises" means "includes." In case of conflict, the present specification, including explanations of terms, will control.

Disclosed herein is a SERS-active PCF probe for use as a biopsy needle and optofluidic sensor.

In one aspect, the present invention relates to a surface-enhanced Raman scattering (SERS)-active photonic crystal fiber (PCF) probe for integrated sample collection and SERS sensing of one or more analytes comprised in the sample, the probe comprising a biopsy needle and a SERS-active PCF integrated into or in communication with the biopsy needle, wherein the PCF has a longitudinal axis and comprises a solid core extending along the length of the longitudinal axis and a cladding region surrounding the solid core, wherein at least the cladding region comprises one or more air holes extending along the longitudinal axis of the PCF, wherein the inner surface of the one or more air holes is functionalized by metallic nanoparticles immobilized thereon that enhance Raman scattering, and the one or more air holes are adapted for SERS sensing of the one or more analytes.

The term "surface-enhanced Raman scattering (SERS)" as used herein refers to a form of Raman spectroscopy, which is based on an inelastic light scattering by molecules (the Raman effect). In the Raman scattering process, a photon interacts momentarily with a molecule and is then scattered into surroundings in all directions. During the brief interaction with molecule, photon loses or gains energy which is then detected and analyzed. An important aspect of the Raman scattering is the correlation between the amount of the frequency shifts and the vibrational modes of the molecules. Here, vibrational modes refer to the "manner" in which the molecule vibrates. Since vibrational modes are sensitive to the chemical nature of the molecule, probing molecular vibrations may thus reveal information regarding its chemical geometry. In SERS, high sensitivity may be achieved by intense enhancement of the local electromagnetic fields in the proximity of a SERS-active material such as a noble metal. Advantageously, its low water background, production of narrower spectral line-widths and no signal bleaching renders it suitability for biological samples analysis.

Photonic crystal fiber (PCF)-based SERS sensing platforms are known in the art. PCFs are optical fibers having a core surrounded by a cladding region having one or more air holes (sometimes called cladding features, inclusions, or microstructures) arranged in a background material, typically in a regular array. Conventional PCFs are optical fibers that employ a microstructured arrangement of a low refractive index material in a background material of a higher refractive index. The background material is typically undoped silica and the low refractive index region is provided by air holes along the whole length of the fiber. Usually, PCFs can be divided into two categories, i.e. high index guiding fibers and low index guiding fibers. Structure-wise, a high index guiding fiber has a solid core with microstructured cladding running along the length of the fiber and a low index guiding fiber has a hollow core and microstructured cladding. The PCFs of the present application have a solid core.

The term "biopsy needle" as used herein refers to relatively slender instruments that can be used to penetrate, and includes instruments having a passage or channel for introducing material into or removing material from a human or animal body.

By including a biopsy needle in the PCF probe of the present application, integrated sample collection and SERS sensing of one or more analytes comprised in the sample is enabled.

The terms "detecting" and "sensing" as used herein refers to a method of determining the presence of an analyte. The technique used to accomplish this is SERS. The detection may also be quantitative, i.e. include correlating the detected signal with the amount of analyte. The detection in the context of the present application includes in vitro as well as in vivo detection.

The term "sample", as used herein, refers to a liquid aliquot of material, frequently biological matrices, an aqueous solution or an aqueous suspension derived from biological material. Non-limiting examples of samples typically used in the methods of the invention include human and animal body fluids such as whole blood, serum, plasma, cerebrospinal fluid, sputum, bronchial washing, bronchial aspirates, urine, semen, lymph fluids and various external secretions of the respiratory, intestinal and genitourinary tracts, wound exudates, tears, saliva, milk, white blood cells, myelomas and the like; and biological fluids such as cell culture supernatants.

The term "analyte" as used herein refers to any substance or object that can be detected in an assay. Therefore, the analyte can be, without limitation, any substance for which there exists a naturally occurring antibody or for which an antibody can be prepared. The analyte may, for example, be an antigen, a protein, a polypeptide, a nucleic acid, a hapten, a carbohydrate, a lipid, a cell, a virus, or any other of a wide variety of biological or non-biological molecules, complexes or combinations thereof. Generally, the analyte will be a protein, peptide, carbohydrate or lipid derived from a biological source such as bacterial, fungal, viral, plant or animal samples. Additionally, however, the target may also be a small organic compound such as a drug, drug-metabolite, dye or other small molecule present in the sample. The analyte of the invention is present in the extracellular space.

Figure 2:
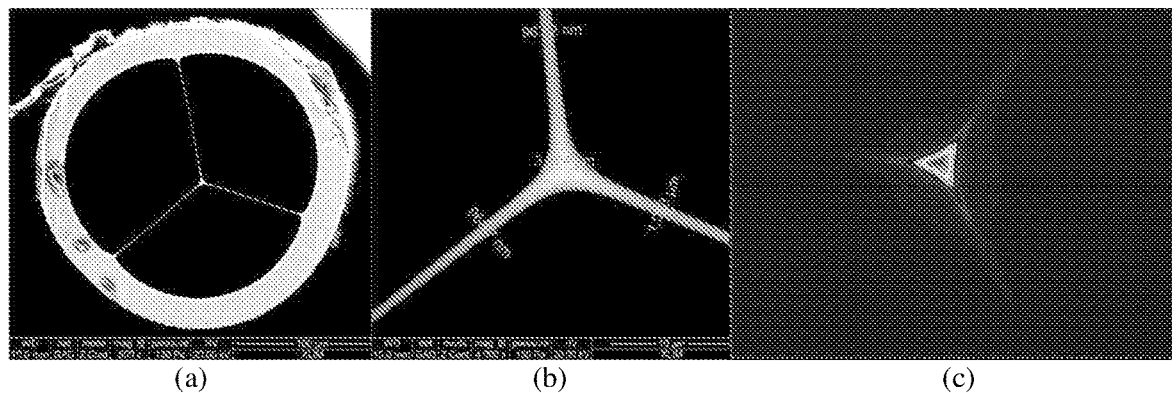
FIG. 2 shows SEM photographs of the cross-section of an optical fiber fabricated by XLIM (a, b) and the distribution of the optical intensity (in near field) at the end of the fiber measured using a CCD camera (c).
Figure 3:
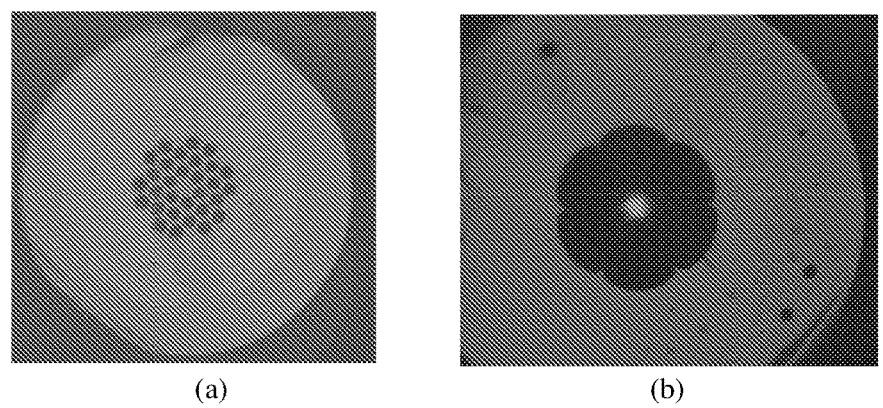
FIG. 3 shows SEM photographs of the cross-section of a typical PCF (a) and an optical fiber composed of small core (hexagonal shape) surrounded six air holes (b). Both optical fibers have been fabricated by XLIM.
Figure 4:
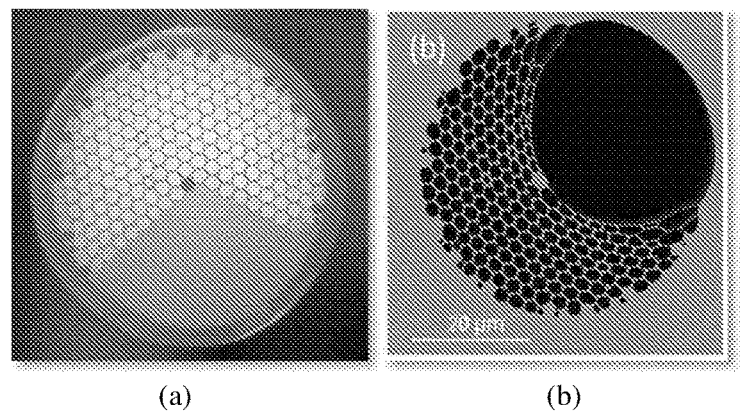
FIG. 4 shows a photograph of the cross-section of the preform of a side-channel PCF (a) and a SEM photograph of the cross-section of a side-channel PCF fabricated by XLIM (b).
Figure 5:
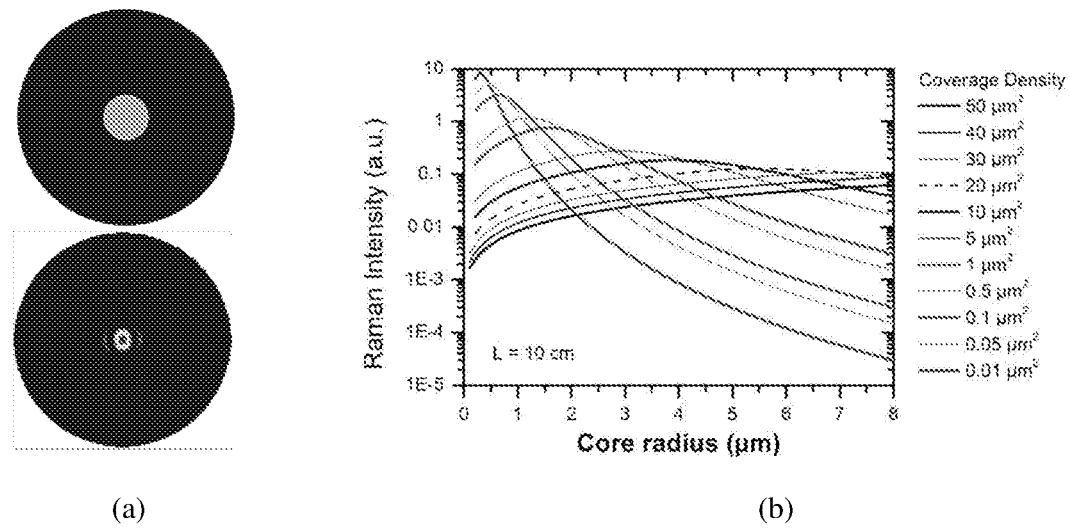
FIG. 5 shows a diagram of the transverse section of the studied functionalized fiber for SERS biosensing, composed of a silica rod surrounded by a layer of gold nanoparticles immersed in water (a, up), the 2D distribution (numerically calculated) of the intensity of the light (wavelength=633 nm) confined in this structure (a, bottom), and the evaluation of the calculated Raman intensity versus the rod radius for different concentration of gold nanoparticle (deposited around the silica rod) for a fiber length of 10 cm (b).
Figure 6:
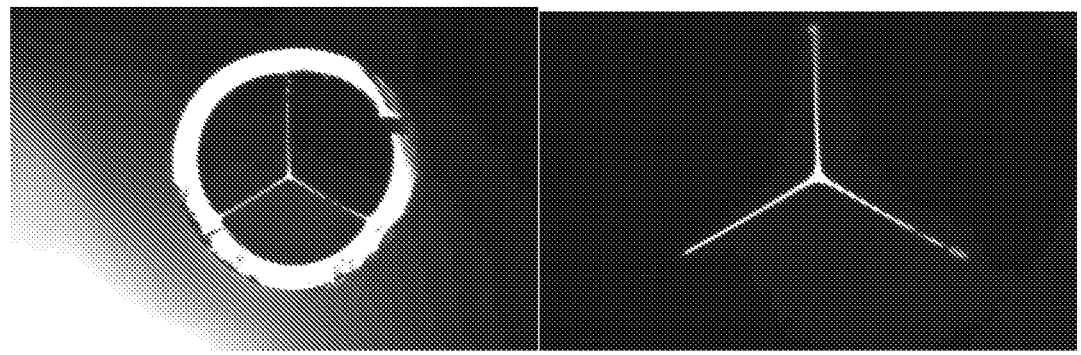
FIG. 6 shows 20× and 50× magnification of 3H-PCF.

In various embodiments, the core and the one or more air holes in the cladding region are arranged in a cross-section pattern as illustrated in, without limitation, any one of FIGS. 2-6 of the drawings. For example, the PCFs of the present application may be a 3-hole fiber PCF as illustrated in FIG. 2 or 6, a side-channel photonic crystal fiber as illustrated in FIG. 4, a typical PCF as illustrated in FIG. 3a, or a hexagonal PCF as illustrated in FIG. 3b.

In preferred embodiments, the one or more air holes are specially designed to have maximum overlap between guided light in the core and leaked (evanescent) light in the air holes for exudates maximum light-analyte interaction to achieve high sensitivity in detection. In addition, the one or more air holes are dimensioned to accommodate the intended sample for analysis.

The optical fiber may for example be made of silica glass. Other materials may be added to the silica glass to alter the refractive index thereof or to provide effects, such as amplification of light, sensitivity, etc. The center-to-center spacing between the cladding holes is defined as the pitch ($\wedge$). The PCFs are usually at least partly characterized by the size of the core and the ratio of the size of the holes to their spacing or pitch ($\wedge$). By tailoring the size and pitch of the cladding holes, the zero-dispersion wavelength (ZDW) of the fiber may be tailored.

In various embodiments, the metallic nanoparticles may assume the form of colloidal metal, hollow or filled nanobars, magnetic, paramagnetic, conductive or insulating nanoparticles, synthetic particles, hydrogel colloids, bars, nanospheres, or nanopillars. Further, the nanoparticles may be single nanoparticles or clusters of nanoparticles.

The metallic nanoparticles may comprise or consist of a SERS-active material. Examples of a SERS-active material include, but are not limited to, noble metals such as silver, palladium, gold, platinum, iridium, osmium, rhodium, ruthenium; copper, aluminum, or alloys thereof. For example, the metallic nanoparticles may be formed entirely from a SERS metal, and may for example, consist of a metal selected from the group consisting of a noble metal, copper, aluminum, and alloys thereof. In various embodiments, the metallic nanoparticles comprise or consist of gold, silver, or alloys thereof. In specific embodiments, the metallic nanoparticles comprise or consist of gold. As another example, the metallic nanoparticles may be formed from a non-SERS active material, such as plastic, ceramics, composites, glass or organic polymers, and coated with a SERS metal such as that mentioned above.

Size of the metallic nanoparticles may be characterized by its diameter. The term "diameter" as used herein refers to the maximal length of a straight line passing through the center of a granule and terminating at the periphery. In embodiments where a plurality of metallic nanoparticles is present, size of the metallic nanoparticles may be characterized by their mean diameter. The term "mean diameter" refers to an average diameter of the nanoparticles, and may be calculated by dividing sum of the diameter of each nanoparticle by the total number of nanoparticles.

In various embodiments, the metallic nanoparticles have a diameter or a mean diameter of about 5 nm to about 250 nm. In some embodiments, the metallic nanoparticle or nanoparticles have a diameter or a mean diameter of about 40 nm to about 100 nm, such as about 50 nm to about 100 nm, about 60 nm to about 100 nm, about 40 nm to about 80 nm, about 40 nm to about 70 nm, about 50 nm to about 70 nm, about 40 nm to about 60 nm, or about 60 nm.

In various embodiments, the metallic nanoparticles comprise or consist of gold nanoparticles having a mean diameter in the range of about 40 nm to about 100 nm. In preferred embodiments, the metallic nanoparticles comprise or consist of gold nanoparticles having a mean diameter of about 60 nm.

Where a plurality of metallic nanoparticles is present, the nanoparticles may be monodispersed. The term "monodispersed" refers to nanoparticles having a substantially uniform size and shape. In some embodiments, the standard deviation of diameter distribution of the metallic nanoparticles is equal to or less than 20% of the mean diameter value, such as equal to or less than 15%, 10%, 5% or 3% of the mean diameter value. In some embodiments, the diameters of the metallic nanoparticles are essentially the same.

In various embodiments, the metallic nanoparticles are immobilized onto the inner surface via a coupling agent, preferably a silane coupling agent, more preferably a molecule comprising a di- or trialkoxysilane group and a functional group capable of binding to the metallic nanoparticles, such as an amino or mercapto group, the coupling agent being preferably selected from (3-mercaptopropyl) trimethoxysilane (MPTMS) and 3-Aminopropyltriethoxysilane (APTES).

In preferred embodiments, the immobilized metallic nanoparticles are further pre-functionalized by a first analyte-binding molecule.

The term "analyte-binding molecule" as used herein refers to any molecule capable of binding to an analyte of choice so as to form a complex consisting of the analyte-binding molecule and the analyte. Preferably, this binding is specific so that a specific complex between analyte and analyte-binding molecule is formed. "Specifically binding" and "specific binding" as used herein mean that the analyte-binding molecule binds to the target analyte based on recognition of a binding region or epitope on the target molecule. The analyte-binding molecule preferably recognizes and binds to the target molecule with a higher binding affinity than it binds to other compounds in the sample. In various embodiments of the invention, "specifically binding" may mean that an antibody or other biological molecule, binds to a target molecule with at least about a $10^4$-fold greater affinity, preferably at least about a $10^6$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. The binding affinity may be determined by any suitable method. Such methods are known in the art and include, without limitation, surface plasmon resonance and isothermal titration calorimetry. In a specific embodiment, the analyte-binding molecule uniquely recognizes and binds to the target analyte.

The analyte-binding molecule may be a proteinaceous molecule, such as an antibody, for example a monoclonal or polyclonal antibody, which immunologically binds to the target analyte at a specific determinant or epitope. The term "antibody" is used in the broadest sense and specifically covers monoclonal antibodies, polyclonal antibodies as well as antibody variants or fragments (e.g., Fab, F(ab')$_2$, scFv, Fv diabodies and linear antibodies), so long as they exhibit the desired binding activity. In various embodiments, the analyte-binding molecule is an antibody, antibody fragment, or antibody-like molecule.

The analyte-binding molecule may also be any other proteinaceous scaffold that has been adapted or mutated to bind a given ligand with sufficient binding affinity. The analyte-binding molecule may also be a binding protein, receptor or extracellular domain thereof capable of forming a binding complex with a ligand, typically a polypeptide or glycopeptide ligand. The analyte-binding molecule can also be a non-proteinaceous receptor, such as for example a nucleic acid based molecule, such as an Aptamer or Spiegelmer (Aptamer made of L-ribonucleotides).

Some metals such as silver, gold, copper, etc. can form covalent bonds with thiol groups. For example, typically the thiol-metal reaction can be used to immobilize an analyte-binding molecule such as an antibody to a gold surface. Also, many proteins can be directly adsorbed onto metal surfaces through non-specific binding. Therefore, combination of adsorption and thiol-gold/silver type of system can be used according to some embodiments of the present invention. By "thiol" is meant a sulfur-containing derivative of an alcohol having a general formula R—SH, where R is an organic radical, for example, a hydrocarbon-derived radical. By "thio" or "thio group" is meant a sulfur-organic group that is derived from a thiol and having a general formula R—S—. The term "non-thio group" refers to a group that is not derived from a thiol.

The first analyte-binding molecule may be immobilized onto the metallic nanoparticles by any means available, such as using a thiol chemistry. In various embodiments, the immobilization comprises immobilizing the first analyte-binding molecule to the metallic nanoparticles by a thiolation step, which preferably comprises converting an original reactive non-thio functional group, e.g. an amino group, a carboxyl group, a carbonyl group, a sulfhydryl/thiol group, or a phosphate group, of the analyte-binding molecules into a thiol group to obtain thiolized molecules for conjugation to metallic nanoparticles.

The term "thiolization" as used herein refers to a process of modification of a molecule, the process comprising introducing the thio group(s) into a molecule not having such groups prior to modification, or increasing the amount of the thio groups in a molecule having some thio groups prior to the modification.

The one or more analytes may be thiolized using a thiolizing agent. Examples of the thiolizing agents that can be employed, depending on which original functional group is being thiolized, include succinimidyl acetylthioacetate (SATA), succinimidyl 3-(2-pyridyldithio)propionate (SPDP), 2-iminothiolane (also known as Traut's reagent), 2,2'-dithio-bis(ethylamine)(cystamine), 3-(2-pyridyldithio) propionyl hydrazide (PDPH), succinimidyl trans-4-(maleimidylmethyl)cyclohexane-1-carboxylate, and 2-acetamido-4-mercaptobutyric acid hydrazide. In one embodiment the process of thiolization can include the activation of the protein prior to thiolization. One example of a reagent that can be used for activation is 1-ethyl-3-(3-dimethylaminopropyl)carbodiimide.

Those having ordinary skill in the art can select suitable thiolizing agents and determine conditions under which the thiolation reaction can be carried out.

The use of the SERS-active PCF probe described herein in a SERS system for SERS biosensing is within the knowledge of the person of average skill in the art.

In another aspect, the invention relates to a method for detecting one or more analytes using surface-enhanced Raman scattering (SERS), the method comprising the steps of:

(i) loading a sample suspected of containing the one or more analytes into a SERS-active PCF probe disclosed herein via the biopsy needle comprised therein;

(ii) immobilizing the one or more analytes to the metallic nanoparticles coated on the one or more air holes of the PCF probe;

(iii) loading a second analyte-binding molecule comprising a Raman reporter moiety into the SERS-active PCF probe; and (iv) detecting the one or more analytes by measuring a SERS signal from the SERS-active PCF probe.

Following introduction of a sample or an aliquot thereof into a SERS-active PCF probe disclosed herein via the biopsy needle comprised therein, the one or more analytes are captured by the first analyte-binding molecule immobilized on the metallic nanoparticles coated on the inner walls of the one or more air holes.

Following analyte capture by the immobilized first analyte-binding molecule, a second analyte-binding molecule comprising a Raman reporter moiety is introduced into the SERS-active PCF probe to contact and selectively bind to the captured analytes, under conditions that allow binding of said second analyte-binding molecule comprising a Raman reporter moiety to an analyte immobilized on the nanoparticles.

The term "Raman reporter moiety" as used herein refers to small organic compounds with distinctive Raman scattering patterns as previously used as Raman spectroscopic reporters, e.g. malachite green isothiocyanate (MGITC), tetramethylrhodamine-5-isothiocyanate (TRITC), X-rhodamine-5-(and-6)-isothiocyanate (XRITC), and 3,3'-diethylthiadicarbocyanine iodide (DTDC), which give rise to characteristic SERS spectra for detection. Methods for conjugating such Raman reporter moiety molecules to aforementioned analyte-binding molecules are known in the art.

It should be understood that the second analyte-binding molecule, which is preferably an antibody specific for the analyte, can bind to the analyte to form a sandwich complex together with the first analyte-binding molecule in a manner such that it does not sterically interfere with the binding of the first analyte-binding molecule to the analyte.

The second analyte-binding molecule comprising a Raman reporter moiety can be in the form of, for example, a nanotag as described in WO2011155901A1, which is hereby incorporated by reference in its entirety.

Figure 13:
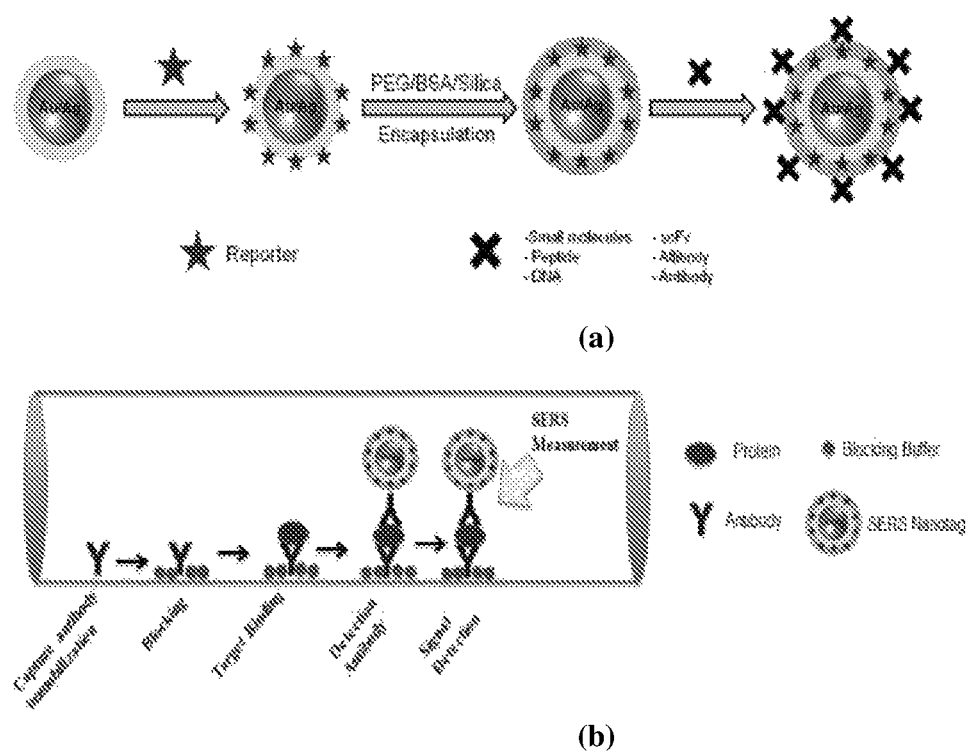
FIG. 13 shows the construction of biofunctionalized SERS Nanotags (a) and targeted detection of proteins/biomarkers in body fluids inside PCF using SERS nanotags (b).

A non-limiting embodiment of this method is illustrated in FIG. 13.

In various embodiments, the method comprises an additional blocking step immediately prior to step (ii).

In various embodiments, the method comprises an additional washing step immediately prior to step (iii) and/or (iv) to remove the unbound analytes and/or analyte-binding molecules, respectively.

In various embodiments, the sample is a body fluid or biological fluid.

In various embodiments, the sample is selected from the group consisting of whole blood, serum, plasma, cerebrospinal fluid, sputum, bronchial washing, bronchial aspirates, urine, semen, lymph fluids, wound exudates, tears, saliva, milk, and cell culture supernatants.

In various embodiments, the one or more analytes are selected from the group consisting of proteins, peptides, nucleic acids, carbohydrates, lipids, small molecules, haptens, cells, and viruses.

In various embodiments, the second analyte-binding molecule is an antibody, antibody fragment, or antibody-like molecule.

In various embodiments, the second analyte-binding molecule is a monoclonal or polyclonal antibody.

In various embodiments, the method is a multiplex method for detecting more than one analyte, wherein in the contacting step more than one analyte-binding molecule is used.

The method of the invention can also be a multiplex method for detecting more than one analyte, i.e. two or more different analytes. This usually requires the use of more than one analyte-binding molecule in the contacting step so that each analyte is bound by a specific analyte-binding molecule.

In various embodiments, the detection is in vivo or in vitro.

It should be understood that other methods may also be used for detecting analytes using the SERS-active PCF probe disclosed herein. For example, the method illustrated in FIG. 12 using direct attachment of the one or more analytes to the nanoparticles, preferably by thiolation, is also within the scope of the present application. In this context, the nanoparticles are not pre-functionalized with analyte-binding molecules. The one or more analytes are attached to the nanoparticles by any means available, preferably by thiolation, followed by recognition and binding by an analyte-binding molecule comprising a Raman reporter moiety.

Without wishing to be bound to any theory, it is believed that the methods disclosed herein can detect analytes in biofluids at ~pM-fM concentrations with nL sample volume.

In still another aspect, the invention relates to the use of the SERS-active PCF probe disclosed herein for the detection of one or more analytes.

In various embodiments, the detection is in vivo or in vitro.

The present invention is further illustrated by the following examples. However, it should be understood, that the invention is not limited to the exemplified embodiments.

EXAMPLES

Materials and Methods

Photonic crystal fibers can be fabricated using different processes such as i) the stack-and-draw, ii) drilled and draw, or iii) extrusion process as known in the art.

The stack-and-draw process comprises drawing glass tube down to capillaries that are stacked together with or without a glass rod, which can be used to form the fiber core (depending on the fiber design). The stack is then inserted into a glass tube. This structure is then drawn down to form a rigid cane composed of air-holes. The cane is then inserted in glass tube that is finally drawn down to an optical fiber (PCF). The fabrication step of a cane could be cancelled depending on the fiber design, meaning that the stack could be directly drawn to fiber. Capillaries could be partially removed along the stack to create an open channel larger than the hole diameter of the capillaries.

The drilled and draw process comprises drilling a large glass rod to from the targeted pattern of air holes according to the fiber design. The drilled rod is then drawn to optical fiber (PCF). An intermediate step could be added; the drilled rod is drawn down to cane that is then inserted into a tube and drawn down to fiber.

The extrusion process comprises pushing melted glass (or several glasses) into a dye and drawing the structured melted glass down to fiber. The dye is designed in a way to obtain the targeted fiber design after the melted glass goes through it. An intermediate step could also be added by fabricating a cane that is then inserted into a glass tube and drawn down to fiber.

The fibers as exemplified herein are fabricated using the stack-and-draw process.

Once the fiber is fabricated, it is functionalized for detecting biomarkers in clinical body fluids will be conducted as per the steps given below such as in Example 2.

Example 1: Fiber Design and Modelling

SERS based biosensing is realized through the interaction between the evanescent parts of the guided light, the nanoparticles (NPs) attached on the fiber inner surface and the analyte. The fraction of evanescent power (i.e. power outside the silica core) depends on the diameter of the core over the operating wavelength (ratio $D_{core}/l$). Smaller the ratio (i.e. core diameter) larger the fraction of evanescent power. Therefore, most of the fiber design tends to the idealistic case of a single rod in air, which is not achievable. This is why most of the fibers are fabricated with a small core hold by few silica struts. The struts are very thin for avoiding parasitic light confinement. Below disclosed is a different fiber design that could be used for SERS based biosensing as a fiber probe and needle biopsy.

The fiber comprises a triangular core held by three thin silica struts (FIG. 2). It is one of the most used fibers because it exhibits three large air holes for fast liquid and analyte infiltration and a small core size and thin struts could be obtained (typically from 4 µm to 0.9 µm, and from 1 µm to 0.4 µm, respectively). The fiber shown in FIG. 3(*a*) is a typical Photonic Crystal Fiber, composed of a hexagonal core shape surrounded by an array of air-holes. This kind of fiber is more favorable for SERS biosensing with high reproducibility and repeatability due to the relative round shape of the core. The fiber shown in FIG. 3(*b*) has a similar core shape (more favorable for high reproducible light coupling into the fiber core) that is hold by six silica struts delimiting six large air holes well suitable for fast liquid infiltration.

The association of both fibers shown in FIG. 3 could be also used as fiber probe needle biopsy for SERS biosensing. This kind of fiber, side-channel PCF (FIG. 4) with one large air hole (channel) compatible with fast liquid infiltration, a small core with a shape well compatible for reproducible and repeatable measurements with a Raman spectrometer, and a photonic crystal cladding that enables additional control of the light properties in the core, such as single mode guiding regime.

The optimization of SERS biosensing performances of the active opto-fluidic fiber biopsy needle depends on the interplay between the length of the fiber sample, the properties of metallic nanoparticles, the coverage density of metallic nanoparticles, the refractive index of the liquid and the size of the fiber core. To realize the optimized scenario, the inventors have adapted a theoretical model to the ideal case of a silica rod in water with gold nanoparticles attached around it. A schematic of the fiber sample cross-section studied in the numerical study is illustrated in FIG. 5(*a*) with a 2D distribution of the pointing vector of the propagated light.

The results illustrated in FIG. 5(*b*) show that the Raman intensity is maximum for a rod radius that depends on the concentration of gold nanoparticles. The value of the optimal radius increases with nanoparticle concentration and vice versa. It should be noted that this experiment did not consider the coupling efficiency between the light (from the Raman spectrometer) and the fiber core.

Example 2: Immobilization of Metallic Nanoparticles Inside the Fiber

Figure 7:
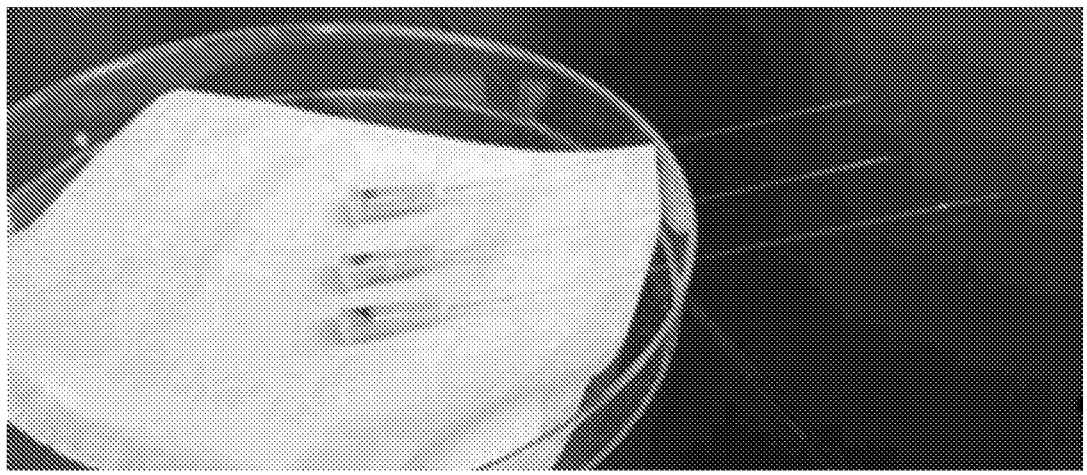
FIG. 7 shows a PCF comprising a biopsy needle.

Prepare approximately about 10 cm of fiber. Strip the cladding and cleave one end of the fiber. In one of the example, the inventors used a 3-hole fiber PCF (3H-PCF) as shown in FIG. 6 below, which is similar to the one shown in FIG. 1. Initially in order to immobilize nanoparticles (NPs), the inventors cleaved the end face of the fiber and take the image of the plain fiber to ensure that it is not contaminated before proceeding with the experiment. The cleaved end will then be connected to 27G needle tip (FIG. 7) and then connected to a syringe pump.

2.1 Cleaning the Fiber

Fiber will be gently washed with acetone or ethanol to remove any trapped impurities. To do this, withdraw acetone or ethanol with a syringe. Place the syringe on the syringe pump and leave it to dispense through the fiber. Next, use an empty syringe to gently push to remove excess liquid out and dry it.

2.2 Functionalizing with Linker

Figure 8:
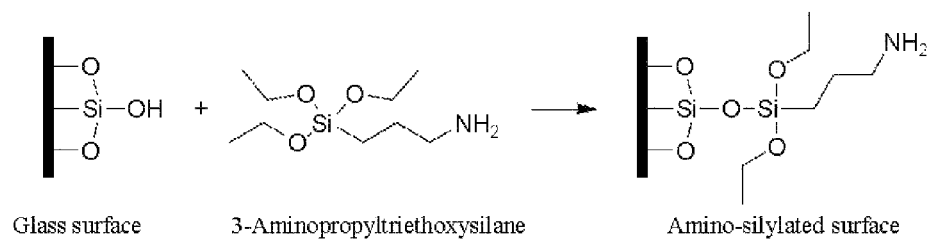
FIG. 8 shows a glass surface functionalized by APTES.

Gold or silver (Ag/Au) NPs are critical in enhancing the Raman signal. It is important to ensure that gold nanoparticles are properly attached to the inner wall of glass fiber in order to obtain the best signal. This is usually done by coating the inner glass wall with a silane containing linker compound (3-mercaptopropyl)trimethoxysilane (MPTMS) or 3-Aminopropyltriethoxysilane (APTES) where such an amino group to functionalize the glass surface. The basic schematic of reaction is shown in FIG. 8.

To realize this inside the fiber, the inventors used a syringe and withdraw APTES linker diluted in acetone at its optimized concentration. The syringe was placed on the pump with the needle attached. It was dispensed at an optimized flow rate and speed and left aside for an optimized time duration for the linker to bind to fiber inner surface. Finally, it is cleaned using the empty syringe to push excess APTES out of the fiber and also washed with pure acetone and dried.

APTES will then act as a linker to bind gold nanoparticles (AuNPs) as the protonated functional group $NH_3^+$ will interact with Ag NPs. The inventors have optimized the concentration of APTES required for optimal functionalization of Au NPs in subsequent step.

2.3 Anchoring Gold Nanoparticles and Washing

Figure 9:
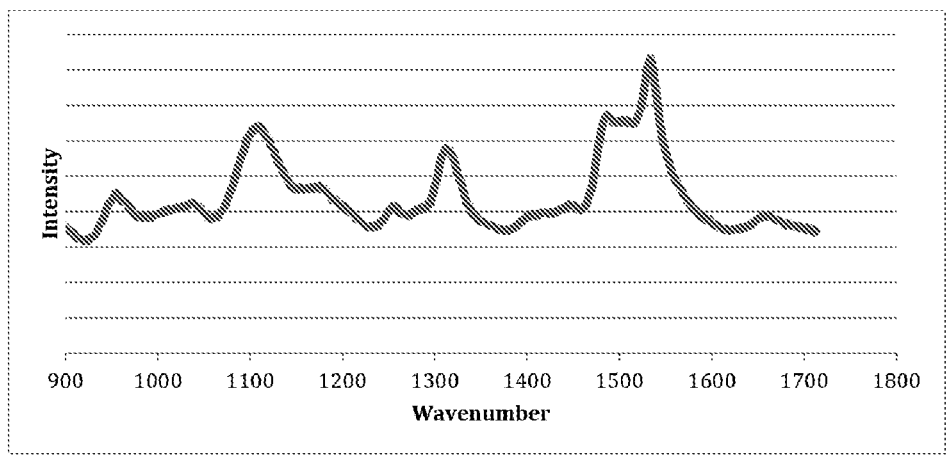
FIG. 9 shows a SERS spectrum from the fiber After Au NPs immobilization.

Use a new syringe and withdraw Au NPs with optimized particle density and leave it to dispense and allow it bind to APTES linker before using an empty syringe to pump excess Au NPs out of the fiber. Finally, fiber is washed with water to remove unbound Au NPs. To do characterization, SERS measurement was taken after this step and the obtained SERS spectra looks like as in FIG. 9.

Figure 10:
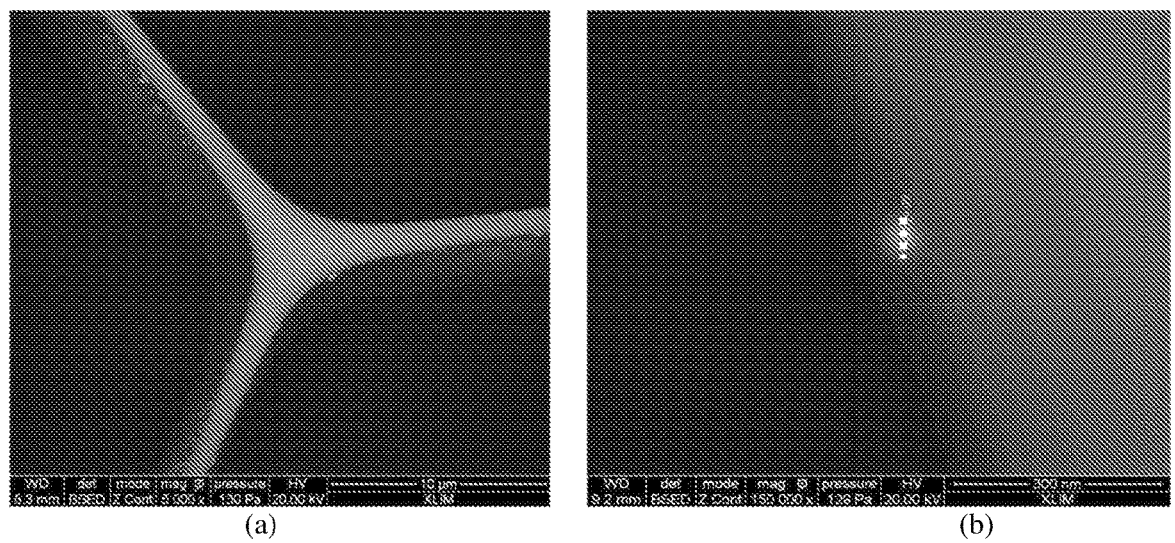
FIG. 10 shows SEM photographs of the cross-section of the optical fiber in which gold nanoparticles with a diameter of 60 nm were immobilized and anchored on the core surface.

As shown in FIG. 10*a*, the inventors also demonstrated by the SEM photographs that the 60 nm NPs are clearly anchored on the inner surface of the core. The measurement of the diameter of the anchored NPs (FIG. 10*b*) confirms the anchoring of NPs.

2.4 Tasting with Raman Reporter Molecules

Figure 11:
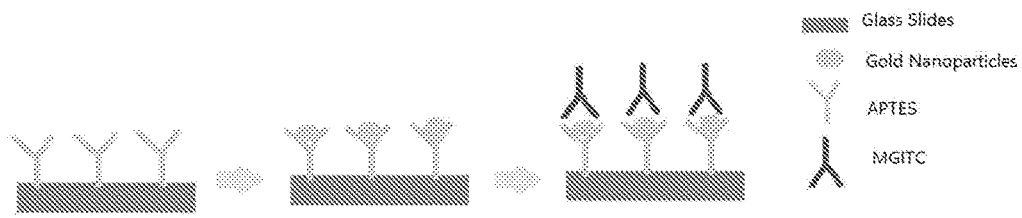
FIG. 11 shows the use of MGITC in SERS detection (a) and a SERS spectrum thereof showing characteristic peaks (b).
Figure 11:
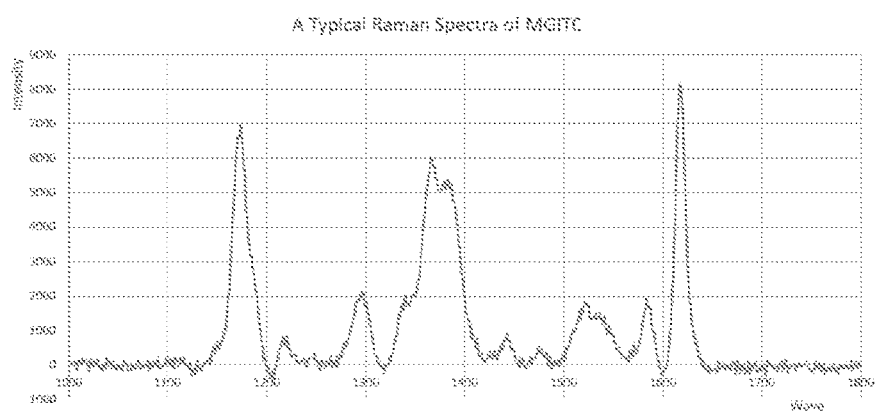

After the anchoring of Au NPs, the PCF will be ready for attaching organic molecules/analytes for sensing. Here as a model molecule, Malachite green isothiocyanate (MGITC) was chosen as the organic Raman reporter molecule (RM). MGITC can bind to Au NPs. The whole process is illustrated by the schematic in FIG. 11*a*. Obtained SERS spectra from bound MGITC showing its characteristic peaks are shown in FIG. 11*b*.

2.5 Attachment of Protein and Washing of Fiber

In order to attach the protein from clinical sample onto the previously anchored NPs inside fiber, a thiolation step was performed. As an example, here, the inventors mixed the sample with 0.5 EDTA (Ethylenediaminetetraacetic acid) and Traunt reagent and incubate for 2 hrs and then centrifuge to get filtrated and concentrated solution. This step introduces thiol group in place of the primary amine part of the protein/biomolecule and thiol group can bind to Au NPs inside the fiber. Then, a syringe pump was used to pump the protein solution up (15 ul) into the fiber connected to the needle and leave it for 30 mins so that the protein can bind to Au NPs. Later, wash the fiber with 1×PBS buffer for 6 mins and pump excess PBS out for 3 mins.

2.6 Pumping Blocking Buffers

Using a new syringe, withdraw blocking buffer and leave it to dispense and leave it inside the fiber. After that use an empty syringe to pump to push out the excess liquid out of the fiber. After the targeted protein is bound to the fiber, the peaks obtained are similar to the AuNPs peaks as in FIG. 8.

2.7 Detecting the Targeted Protein Using Antibody Linked Raman Reporter Probe

Figure 12:
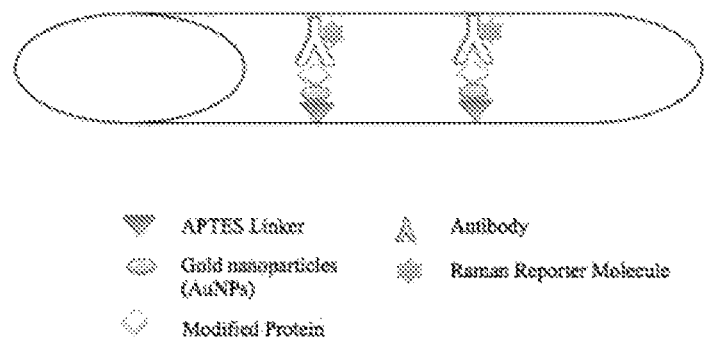
FIG. 12 shows a schematic illustration of fiber functionalization for targeted protein binding in clinical fluid.

The inventors used highly Raman active Aminothiophenol (ATP) as a reporter molecule (RM). Anchoring of antibody of the targeted protein to a reporter molecule (RM) is realized through the EDC-NHC coupling reaction. After the mixing of EDC, NHS and RM at its optimized concentration with antibody, it is centrifuged and concentrated the filtered solution. This RM-anchored antibody is subsequently introduced into the fiber needle through the syringe pump to target the bound protein from clinical sample followed by necessary washing. When SERS measurement was carried out, signal intensity from RM will indicate the amount of targeted protein. The overall functionalized fiber scheme is shown in FIG. 12.

Example 3: Detection of Proteins Using Sandwich Method

Detection of disease biomarkers in body fluids, which generally have very low Raman scattering cross-section can also be realized by sandwich method with SERS nanotags (SERS active nanoparticle tags) as sensing probes. SERS nanotags are realized by anchoring strong RMs onto the surface of metal NPs, which can be further conjugated with molecular recognition motifs for specific targeted detection (FIG. 13*a*). Targeted biomarker's capturing primary antibody is first immobilized on the inner walls of the air hole using established protocol. Then the body fluid sample is pumped into the fibre and the biomarker of interest is captured by the primary antibody. After necessary washing to remove the unbound targeted proteins, SERS nanotags with a corresponding secondary antibody, which act as the sensing SERS probe, are introduced into the fibre (FIG. 13*b*). The amount of SERS signal obtained from the targeted SERS nanotags is directly related to the concentration of the biomarker present in the sample.

Example 4: Detection of Ovarian Cancer Biomarker, Haptoglobin from Cyst Fluid

Figure 14:
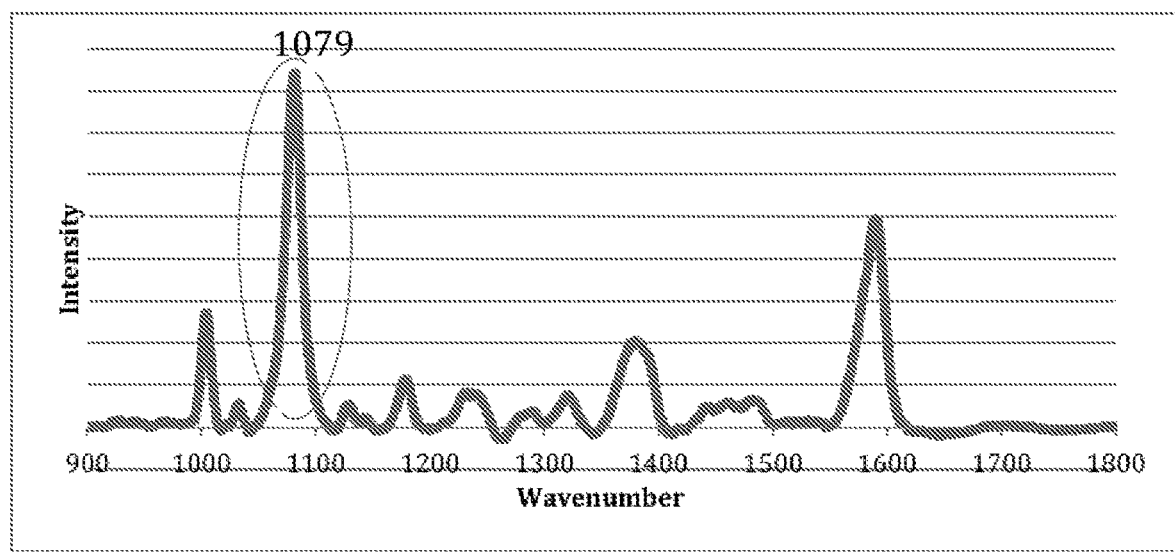
FIG. 14 shows a SERS spectrum after antibody incubation.
Figure 15:
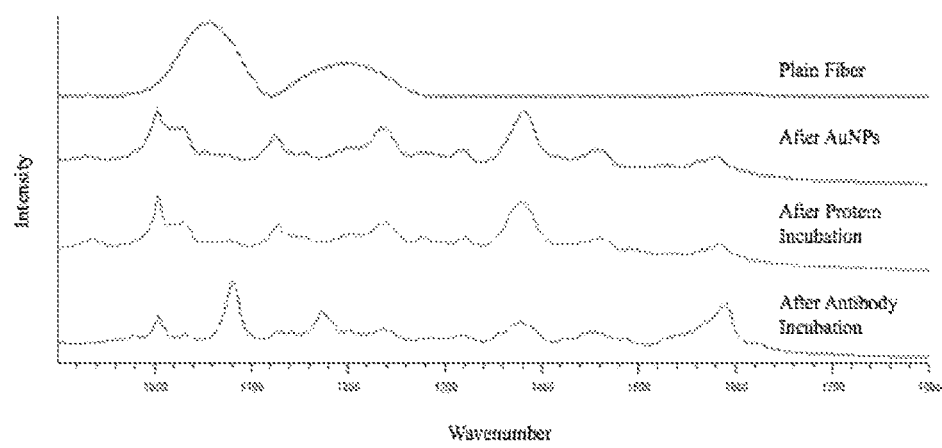
FIG. 15 shows SERS spectra from 3H-SCPCF after different stages of functionalization.
Figure 16:
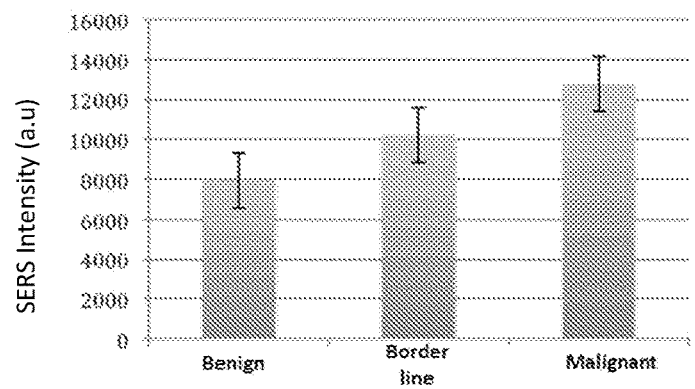
FIG. 16 shows SERS intensity of haptoglobin from cyst fluid differentiating benign and malignant ovarian cyst.

For the first time, the inventors detected the presence of haptoglobin, a biomarker for ovarian cancer from clinical cyst fluid using the functionalization approach in section 2.5-2.7 of Example 2. The level of haptoglobin is indication of benign and malignant state of tumor. The inventors have tested the cyst fluid collected from patients using functionalized PCF biopsy needle probe as in section 2.7. SERS spectra that were obtained were baseline subtracted and the peak intensity at ~1079 $cm^{-1}$ of ATP (FIG. 14) was averaged and compared among the three different concentrations of sample such as benign, borderline malignant and malignant. Further, SERS spectra from fiber at different stage of functionalization is shown in FIG. 15. It shows that after the specific binding of haptoglobin antibody with ATP linker to the protein showed distinct peak for the ATP.

Figure 17:
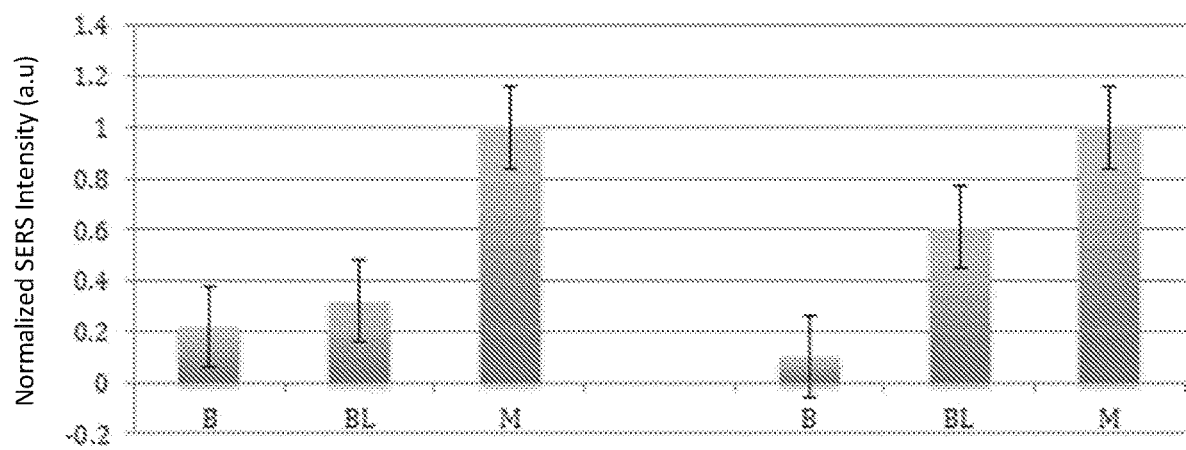
FIG. 17 shows normalized SERS intensity of haptoglobin from cyst fluid differentiating benign and malignant ovarian cyst. The experiment was repeated twice as indicated.

Average of measurements from 7 sets of samples repeated twice are shown in FIG. 17. In the figure, B represents Benign, BL: Border line and M is malignant.

Example 5: Detection of Wound Biomarker, MMP9

Figure 18:
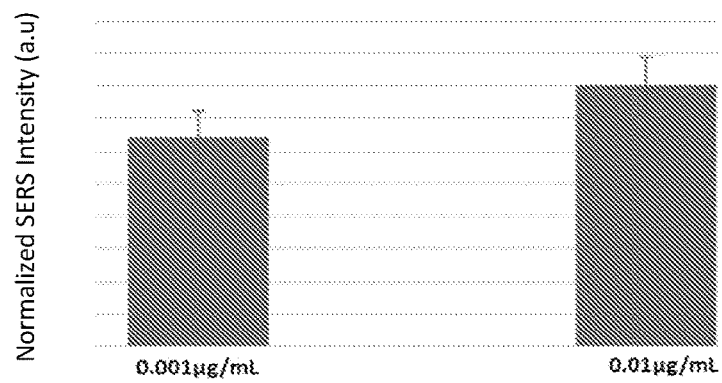
FIG. 18 shows normalized SERS intensity indicating the detection of different levels of MMP 9 using aminothiophenol.

As in Example 4, the inventors also detected the MMP 9 protein, which has high relevance in determining healing status of chronic wound. As shown in FIG. 18, the inventors could detect the different concentration of MMP 9 using the fiber biopsy needle.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A surface-enhanced Raman scattering (SERS)-active photonic crystal fiber (PCF) probe for integrated sample collection and SERS sensing of one or more analytes comprised in the sample, the probe comprising a biopsy needle and a SERS-active PCF integrated into or in communication with the biopsy needle,
wherein the PCF has a longitudinal axis and comprises a solid core extending along the length of the longitudinal axis and a cladding region surrounding the solid core, wherein at least the cladding region comprises one or more air holes extending along the longitudinal axis of the PCF,
wherein the inner surface of the one or more air holes is functionalized by metallic nanoparticles immobilized thereon that enhance Raman scattering, and the one or more air holes are adapted for SERS sensing of the one or more analytes.

2. The SERS-active PCF probe of claim 1, wherein the core and the one or more air holes in the cladding region are arranged in a pattern.

3. The SERS-active PCF probe of claim 1, wherein the inner surface of the one or more air holes comprises, consists essentially of or is made of silica glass.

4. The SERS-active PCF probe of claim 1, wherein the metallic nanoparticles comprise or consist of a noble metal or copper.

5. The SERS-active PCF probe of claim 4, wherein the noble metal is gold or silver.

6. The SERS-active PCF probe of claim 1, wherein the metallic nanoparticles have a mean diameter in the range from 5 nm to 250 nm.

7. The SERS-active PCF probe of claim 1, wherein the metallic nanoparticles comprise or consist of gold nanoparticles having a mean diameter of 60 nm.

8. The SERS-active PCF probe of claim 1, wherein the metallic nanoparticles are immobilized onto the inner surface via a coupling agent.

9. The SERS-active PCF probe of claim 1, wherein the metallic nanoparticles are further functionalized by a first analyte-binding molecule immobilized thereon.

10. The SERS-active PCF probe of claim 9, wherein the first analyte-binding molecule is an antibody, antibody fragment, or antibody-like molecule.

11. A method for detecting one or more analytes using surface-enhanced Raman scattering (SERS), the method comprising the steps of:
(i) loading a sample suspected of containing the one or more analytes into a SERS-active PCF probe of claim 1 via the biopsy needle comprised therein;
(ii) immobilizing the one or more analytes to the metallic nanoparticles coated on the one or more air holes of the PCF probe;
(iii) loading a second analyte-binding molecule comprising a Raman reporter moiety into the SERS-active PCF probe; and
(iv) detecting the one or more analytes by measuring a SERS signal from the SERS-active PCF probe.

12. The method of claim 11, wherein the method comprises an additional blocking step immediately prior to step (ii).

13. The method of claim 11, wherein the method comprises an additional washing step immediately prior to step (iii) and/or (iv) to remove the unbound analytes and/or analyte-binding molecules, respectively.

14. The method of claim 11, wherein the sample is a body fluid or biological fluid.

15. The method of claim 11, wherein the sample is selected from the group consisting of whole blood, serum, plasma, cerebrospinal fluid, sputum, bronchial washing, bronchial aspirates, urine, semen, lymph fluids, wound exudates, tears, saliva, milk, and cell culture supernatants.

16. The method of claim 11, wherein the one or more analytes are selected from the group consisting of proteins, peptides, nucleic acids, carbohydrates, lipids, small molecules, haptens, cells, and viruses.

17. The method of claim 11, wherein the second analyte-binding molecule is an antibody, antibody fragment, or antibody-like molecule.

18. The method of claim 11, wherein the Raman reporter moiety comprised in the second analyte-binding molecule is selected from the group consisting of malachite green isothiocyanate (MGITC), tetramethylrhodamine-5-isothiocyanate (TRITC), X-rhodamine-5-(and-6)-isothiocyanate (XRITC), and 3,3'-diethylthiadicarbocyanine iodide (DTDC).

19. The method of claim 11, wherein the method is a multiplex method for detecting more than one analyte, wherein in the contacting step more than one analyte-binding molecule is used.

20. The method of claim 11, wherein the detection is in vivo or in vitro.

* * * * *